United States Patent
Takahashi et al.

(10) Patent No.: US 6,231,585 B1
(45) Date of Patent: May 15, 2001

(54) DEVICE FOR STABILIZING A TREATMENT SITE AND METHOD OF USE

(75) Inventors: Masao Takahashi, Chigasaki (JP); Elazer E. Edelman, Brookline, NJ (US); Kenneth W. Carpenter, Del Mar, CA (US)

(73) Assignee: Medivas, LLC, La Jolla, CA (US)

( * ) Notice: Subject to any disclaimer, the term of this patent is extended or adjusted under 35 U.S.C. 154(b) by 0 days.

(21) Appl. No.: 09/328,526

(22) Filed: Jun. 9, 1999

Related U.S. Application Data

(63) Continuation-in-part of application No. 09/293,334, filed on Apr. 16, 1999, which is a continuation-in-part of application No. 09/171,774, filed on Oct. 26, 1998, now Pat. No. 6,071,295, and a continuation-in-part of application No. PCT/JP97/04230, filed on Feb. 27, 1997.

(51) Int. Cl.[7] .................................................. A61M 29/00
(52) U.S. Cl. ............................................................. 606/191
(58) Field of Search ..................................... 606/191, 108, 606/15, 16, 19; 604/176, 95.04, 95.01, 95.05, 522, 902; 128/897, 898, 899; 607/6–14

(56) References Cited

U.S. PATENT DOCUMENTS

| 3,720,433 | 3/1973 | Rosfelder | 294/64 |
|---|---|---|---|
| 3,858,926 | 1/1975 | Ottenhues | 294/64 |
| 4,047,532 | 9/1977 | Phillips et al. | 128/303 |

(List continued on next page.)

FOREIGN PATENT DOCUMENTS

| 293760 | 8/1916 | (DE) . | |
|---|---|---|---|
| 0 357 338 A2 | 8/1989 | (EP) | A61M/1/36 |
| WO 94/18881 | 9/1994 | (WO) | A61B/1/00 |
| WO 95/01757 | 1/1995 | (WO) | A61B/19/00 |
| WO 95/15715 | 6/1995 | (WO) | A61B/8/12 |
| WO 96/00033 | 1/1996 | (WO) | A61B/17/00 |

OTHER PUBLICATIONS

Fanning et al., "Reoperative Coronary Artery Bypass Grafting Without Cardiopulmonary Bypass," *The Annals of Thoracic Surgery*, 55:486–489 (1993).

Th. Lavergne et al., "Transcatheter Radiofrequency Ablation of Atrial Tissue Using a Suction Catheter," *PACE*, 12:177–186 (1989).

Trapp and Bisarya, "Placement of Coronary Artery Bypass Graft Without Pump Oxygenator," *The Annals of Thoracic Surgery*, 19(1):1–9 (1975).

Primary Examiner—Henry J. Recla
Assistant Examiner—Vy Q. Bui
(74) Attorney, Agent, or Firm—Gray Cary Ware & Freidenrich LLP; June M. Learn

(57) ABSTRACT

The present invention provides stabilizing devices and methods of use for temporarily remotely immobilizing a local area of tissue, such as a local area of tissue on a beating heart, or other internal organ, to thereby permit minimally-invasive or robotic surgery thereon. The invention stabilizing device, which is coupled to a vacuum source, features an elastomeric suction body mounted on the steerable tip of a rod-like instrument, such as a steerable catheter. The flexible or steerable tip and elongate suction channel are sized for introduction into an interior body cavity via a small surgical opening. A steering mechanism mounted at the proximal end of the device is used to coil the elongate tip and suction channel into a ring- or horseshoe-shape within the body cavity. Preferably, the suction channel has a flexible, spreadable outer rim portion which is designed to flatten and spread outwardly against the surface of the treatment site as air is withdrawn from the coiled suction channel to distribute the pressure against the treatment site while maximizing the suction field. The suction body is manufactured of a soft, compliant material, such as an elastomeric polymer, to allow the suction channel to be transformed into the coiled conformation without deformation sufficient to defeat its purpose of use, i.e., clinging to the surface of a treatment site under partial vacuum.

44 Claims, 2 Drawing Sheets

U.S. PATENT DOCUMENTS

| | | | |
|---|---|---|---|
| 4,368,736 | 1/1983 | Kaster | 128/334 |
| 4,627,421 | 12/1986 | Symbas et al. | 128/20 |
| 4,637,377 | 1/1987 | Loop | 128/1 R |
| 4,646,747 | 3/1987 | Lundback | 128/643 |
| 4,718,418 | 1/1988 | L'Esperance, Jr. | 128/303.1 |
| 4,736,749 | 4/1988 | Lundback | 128/643 |
| 4,766,907 | 8/1988 | de Groot et al. | 128/754 |
| 4,808,163 | 2/1989 | Laub | 604/105 |
| 4,854,318 | 8/1989 | Solem et al. | 128/346 |
| 4,865,019 | 9/1989 | Phillips | 128/20 |
| 4,960,134 | 10/1990 | Webster, Jr. | 128/786 |
| 4,962,758 | 10/1990 | Lasner et al. | 128/41 |
| 4,989,587 | 2/1991 | Farley | 128/20 |
| 4,991,578 | 2/1991 | Cohen | 128/419 |
| 5,009,660 | 4/1991 | Clapham | 606/166 |
| 5,011,469 | 4/1991 | Buckberg et al. | 604/4 |
| 5,053,041 | 10/1991 | Ansari et al. | 606/148 |
| 5,108,412 | 4/1992 | Krumeich et al. | 606/166 |
| 5,151,086 | 9/1992 | Duh et al. | 604/51 |
| 5,167,223 | 12/1992 | Koros et al. | 128/20 |
| 5,171,254 | 12/1992 | Sher | 606/166 |
| 5,190,050 | 3/1993 | Nitzche . | |
| 5,287,861 | 2/1994 | Wilk | 128/898 |
| 5,365,921 | 11/1994 | Bookwalter et al. | 128/20 |
| 5,372,124 | 12/1994 | Takayama et al. | 128/4 |
| 5,374,277 | 12/1994 | Hassler | 606/207 |
| 5,420,698 | 5/1995 | Suzuki et al. | 358/474 |
| 5,425,705 | 6/1995 | Evard et al. | 604/28 |
| 5,437,651 | 8/1995 | Todd et al. | 604/313 |
| 5,441,507 | 8/1995 | Wilk | 606/139 |
| 5,472,438 | 12/1995 | Schmit et al. | 606/1 |
| 5,509,890 | 4/1996 | Kazama | 600/37 |
| 5,545,123 | 8/1996 | Ortiz et al. | 600/235 |
| 5,549,542 | 8/1996 | Kovalcheck | 600/146 |
| 5,613,937 | 3/1997 | Garrison et al. | 600/201 |
| 5,626,609 | 5/1997 | Zvenyatsky et al. | 606/208 |
| 5,725,523 * | 3/1998 | Mueller | 606/15 |
| 5,727,569 | 3/1998 | Benetti et al. | 128/898 |
| 5,779,646 | 7/1998 | Koblish et al. | 600/567 |
| 5,782,860 | 7/1998 | Epstein et al. | 606/213 |
| 5,807,377 | 9/1998 | Madhani et al. | 606/1 |
| 5,836,311 | 11/1998 | Borst et al. | 128/897 |
| 5,846,183 | 12/1998 | Chilcoat | 600/136 |
| 5,875,782 | 3/1999 | Ferrari et al. | 128/898 |
| 5,876,373 | 3/1999 | Giba et al. | 604/95 |
| 5,888,247 | 3/1999 | Benetti | 623/66 |
| 5,894,843 | 4/1999 | Benetti et al. | 128/898 |
| 5,906,607 | 5/1999 | Taylor et al. | 606/1 |

\* cited by examiner

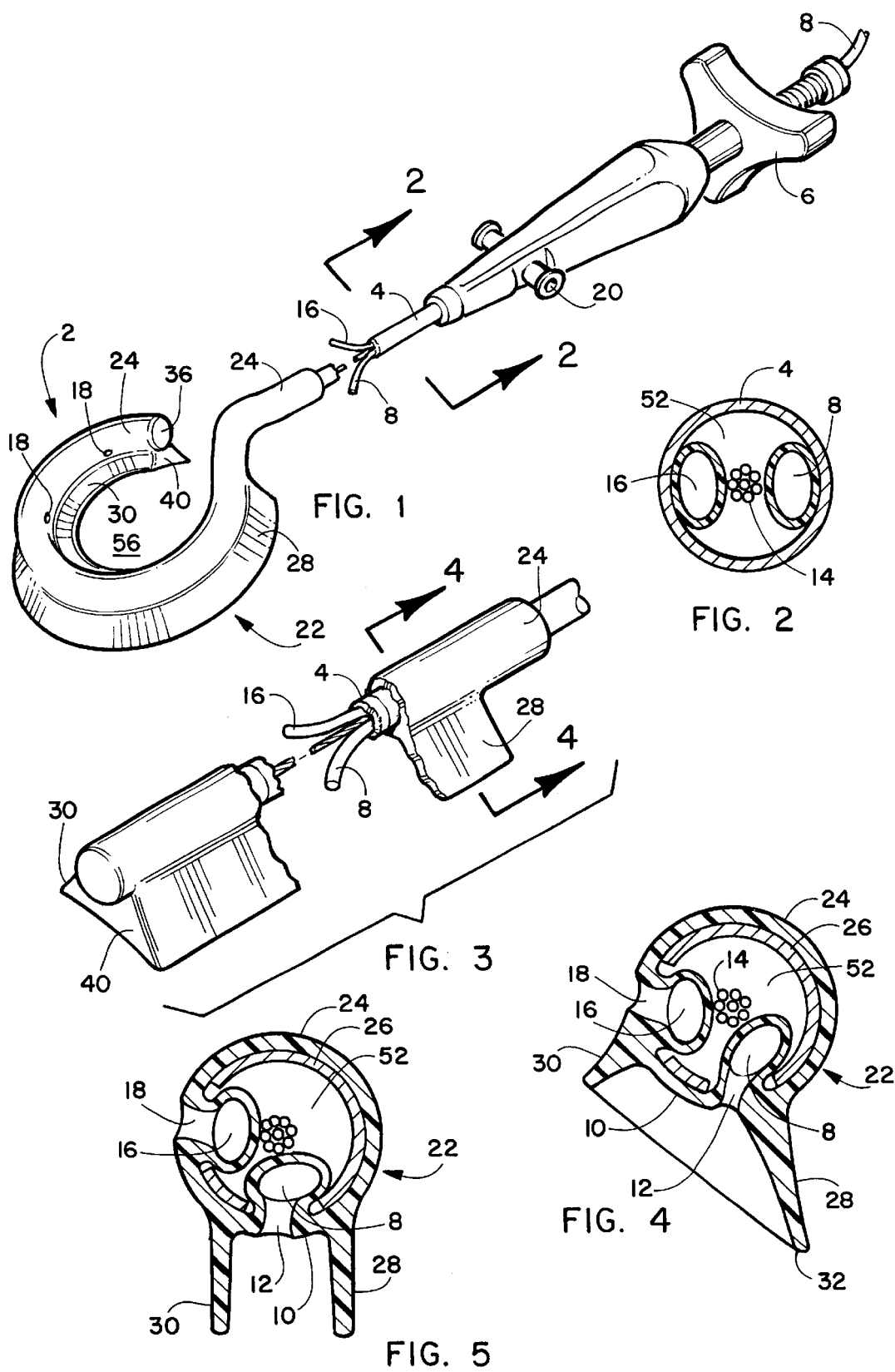

DEVICE FOR STABILIZING A TREATMENT SITE AND METHOD OF USE

RELATED APPLICATIONS

This application is a continuation-in-part application of U.S. patent application Ser. No. 09/293,334, filed Apr. 16, 1999, which is a continuation in part of U.S. patent application Ser. No. 09/171,774, filed Oct. 26, 1998 now U.S. Pat. No. 6,071,295; which derives priority from PCT Application No. JP97/04230, filed on Feb. 27, 1997, all of which are incorporated herein by reference in their entireties.

FIELD OF THE INVENTION

The present invention generally relates to surgery on body tissues and organs. More specifically, the present invention relates to a method and apparatus for temporarily immobilizing a local area of tissue within a body cavity subject to motion, such as the heart wall, which permits an endoscopic or robotic treatment procedure to be performed on that local area of tissue.

BACKGROUND OF THE INVENTION

Coronary artery disease remains the leading cause of morbidity and mortality in Western societies and is manifested in a number of ways. For example, disease of the coronary arteries can lead to insufficient blood flow to various areas of the heart. This can lead to the discomfort of angina and the risk of ischemia. In severe cases, acute blockage of coronary blood flow can result in irreversible damage to the myocardial tissue, including myocardial infarction and the risk of death.

A number of approaches have been developed for treating coronary artery disease. In less severe cases, it is often sufficient to merely treat the symptoms, with pharmaceuticals, or treat the underlying causes of the disease, with lifestyle modification. In more severe cases, the coronary blockage can be treated endovascularly or percutaneously using techniques such as balloon angioplasty, atherectomy, laser ablation, stents, and the like.

In cases where these approaches have failed or are likely to fail, it is often necessary to perform a coronary artery bypass graft procedure. This procedure generally involves opening the chest by median sternotomy, spreading the left and right rib cage apart; and opening the pericardial sac to achieve direct access to the heart. Next, a blood vessel or vessels for use in the graft procedure are mobilized from the patient. This usually entails mobilizing either a mammary artery or a saphenous vein, although other graft vessels may also be used.

Commonly, a heart-lung or cardiopulmonary bypass is performed so that the beating of the heart can be stopped during the surgical procedure. This usually entails arterial and venous cannulation, connecting the bloodstream to a heart-lung machine, cooling the body to about 32 degrees Celsius, cross-clamping of the aorta and cardioplegic perfusion of the coronary arteries to arrest and cool the heart to about 4 degrees Celsius. The arrest or stoppage of the heart is generally required because the constant pumping motion of the beating heart would make surgery upon the heart difficult in some locations and extremely difficult if not impossible in other locations Once cardiac arrest is achieved, a graft (or grafts) is attached to the relevant portions of a coronary artery (or arteries) followed by weaning from the cardiopulmonary bypass, restarting the heart, and decannulation. Finally the chest is closed.

However, use of the cardiopulmonary bypass may create difficulties for the patient and increase the expense and time required for the procedure. In a cardiopulmonary bypass, all the patient's blood, which normally returns to the right atrium, is diverted to a system which supplies oxygen to the blood, removes carbon dioxide, and returns the blood, at sufficient pressure, into the patient's aorta for further distribution into the body. Generally, such a system requires several separate components, including an oxygenator, several pumps, a reservoir, a blood temperature control system, filters, and flow, pressure, and temperature sensors.

Due to the risks incurred during cardiopulmonary bypass, others have attempted to perform a coronary artery bypass graft procedure without cardiac arrest and cardiopulmonary bypass in a procedure known as an "off pump coronary artery bypass" (OPCAB) procedure. For example, Trapp and Bisarya (*Annals Thorac. Surg.* 19(1):1–9, 1975) immobilized the area of the bypass graft by encircling sutures deep enough to incorporate enough muscle to suspend an area of the heart while preventing damage to the coronary artery. More recently, Fanning et al (*Annals Thorac. Surg.* 55: 486–489, 1993) reported immobilizing the area of the bypass graft with stabilization sutures.

While these attempts have achieved some success, they generally require enhanced skill of the surgeon to properly create the anastomosis because, even with use of sutures to suspend a portion of the surface of the heart upon which the surgery is conducted, the beating heart continues to move more than desired in the relevant area. In addition, the sutures may cause a myocardial tear, an injury of the coronary artery branches, or such complications as embolism or focal arteriosclerosis resulting from the pressures of the ligatures upon the artery.

In order to solve such problems associated with the use of sutures to stabilize the site of an anastomosis upon the surface of a beating heart, a device known as a "local myocardial compression device" has been developed wherein myocardial portions on both sides of the coronary artery on which anastomosis is to be performed are compressed with a two-tined fork-like instrument to apply pressure upon the artery and the heart itself so as to stabilize the treatment site. While use of this device has met with some success, the application of local compression to the heart can effect considerable local deterioration of cardiac function, particularly when cardiopulmonary bypass is not used to supplement blood circulation. In addition, this device does not address the problem of bleeding from a locally dissected coronary artery intended for anastomosis.

To address the undesirable effect of compression of the heart, such as is caused by use of the local myocardial compression device, a suction-assisted device has been developed. The suction-assisted device has two paddles, each of which includes a series of suction ports located at the point where the device interfaces with the surface of the heart, as described in U.S. Pat. No. 5,836,311. The paddles are applied to the surface of the heart across an arterial section intended as an anastomotic site and suction applied through the suction ports is employed to lift and hold the surface tissue of a beating heart at the anastomotic site to minimize motion of the treatment site while the heart continues to beat underneath. This device may be used in either a conventional, open-chest environment or in an endoscopic minimally invasive procedure. However, it has been discovered that application of pressure at localized points using such a device can cause suction induced hemorrhages on the surface of the heart that result in scarring of the heart.

The need for stabilization of a moveable surgical or biopsy site (i.e., a treatment site) is not limited to the case of the beating heart. Robotic surgery is presently being conducted on a number of internal organs. Such surgeries would be enhanced by a stabilizing device that could be inserted through a small surgically created opening to control the movement or otherwise stabilize the surgical site to aid in visualization and manipulation of the surgical site remotely, i.e., during robotic surgery.

A number of minimally invasive surgical (MIS) techniques have been developed to minimize both the time required for surgery or diagnosis and the size of the surgical opening created in the patient's body. To perform MIS, the surgeon uses special instruments that allow the surgeon to maneuver inside the patient. One type of instrument that is used in minimally invasive surgery is forceps, an instrument having a tip specifically configured to grasp objects, such as needles. Because forceps and other instruments designed for minimally invasive surgery are generally long and rigid, they may fail to provide a surgeon the dexterity and precision necessary to effectively carry out many procedures in a minimally invasive fashion that requiring extensive delicate suturing. This problem is increased if the surgical site is in motion during MIS due its anatomical location, such as the surface of a beating heart.

Robotic systems for use in surgery are being developed to increase a surgeon's dexterity as well as to allow a surgeon to operate on a patient from a remote location. In these robotic systems, the surgeon uses some form of servomechanism, usually computer driven, to manipulate the movements of the surgical instruments rather than directly holding and moving the tools. In such a system, the surgeon is provided with an image of the patient's body at the remote location. A viewing instrument, typically including a miniaturized video camera, is inserted into the body part through a small surgical opening and a variety of surgical instruments and retractors can be inserted through others. The image provided by the viewing device may be displayed on a video screen or television monitor, affording the surgeon enhanced visual control over the instruments. While viewing the three-dimensional image, the surgeon performs the surgical procedures on the patient by manipulating a master device that controls the motion of a servomechanism-actuated instrument. The surgeon's hands and the master device are positioned relative to the image of the operation site in the same orientation as the instrument is positioned relative to the act. During the operation, the instrument provides mechanical actuation and control of a variety of surgical instruments, such as tissue graspers, needle drivers, etc., that each perform various functions for the surgeon, i.e., holding or driving a needle, grasping a blood vessel or dissecting tissue. An overview of the state of the art with respect to robotic surgery technology can be found in "Computer Integrated Surgery: Technology And Clinical Applications" (MIT Press, 1996). Moreover, systems for telesurgery are described in U.S. Pat. Nos. 5,417,210, 5,402,801, 5,397,323, 5,445,166, 5,279,309, 5,299,288.

The robotic system may also be more highly automated. The imaging device may be a computerized tomography (CT) axial imaging system, a magnetic resonance imaging (MRI) device, or any suitable imaging system that provides information regarding the structure of the bodily location to be operated on. The robotic arm is utilized to precisely orient the surgical tools or other implements used in conducting the surgery or related procedure and a control means, such as a computer, utilizes information received from the imaging device, alone or together with other information, to control the robotic arm. Such image-assisted robotic surgery is described in U.S. Pat. No. 5,078,140.

The instruments used in such limited spaces, such as an instrument that could be used to stabilize a treatment site, are necessarily designed for ease of insertion through a small opening and for remote manipulation. Thus, there is a need in the art for new and better devices and methods of using them to stabilizing a surgical site, such as the surface of the beating heart, or for stabilizing a an interior therapeutic or diagnostic treatment site during minimally invasive or robotic surgery.

SUMMARY OF THE INVENTION

In accordance with the present invention, there are provided devices for stabilizing the surface of a treatment site within a body cavity of a subject. The invention stabilizing device features a flexible coilable suction channel attached to a steerable rod that can be advanced into a body cavity of a subject through a small surgical opening in an open, elongate form and then transformed within the body of the subject into coiled form for attachment to the surface of an internal treatment site, such as an internal organ, by introduction of a partial vacuum into the suction channel while the suction channel is held against the surface of the treatment site (i.e., in the coiled form). Thus, the invention stabilizing device is particularly suited for stabilizing the surface of a treatment site within a body cavity of a subject during robotic surgery.

The invention stabilizing device comprises an elongate hollow rod having a proximal end and a distal end with a flexible portion at the distal tip thereof, with the rod being sized and constructed to be advanced into a body cavity of a subject. The invention device further comprises a deflection mechanism attached to the flexible portion of the rod and to a steering mechanism associated with the proximal end of the rod for causing the flexible portion of the rod to coil into a ring- or horseshoe-shape. Attached to the flexible tip of the rod in the invention device is an elongate coilable suction channel comprising an elongate base attached along one side of the flexible tip, a flexible rim surrounding the perimeter of the base on the side opposite to the attachment of the base to the flexible tip, and one or more suction ports in the suction channel adapted to receive a partial vacuum from a remote source. Actuation of the steering mechanism in the invention device causes the suction channel to coil into a ring- or horseshoe-shape.

For introducing a partial vacuum into the suction channel, the hollow rod generally houses, in addition to the steering assembly (i.e., the deflection mechanism and the steering mechanism), at least one lumen, for example a suction tubing in fluid communication between the one or more suction ports in the suction channel and a source of partial vacuum In a preferred embodiment, the tip of the rim is flared and flexible along the portion of the rim that runs along the outer perimeter of the base when the suction channel is in the coiled orientation so that application of a partial vacuum to the suction channel while the rim is in contact with the treatment site causes the flared outer rim portion to flatten and spread outwardly across the surface of the treatment site. By this means a soft edge for the suction channel is created to avoid bruising of the underlying tissue. As the spreading of the outer rim portion also enlarges the suction field to apply the partial vacuum over an increased tissue area, localized hemorrhage (e.g., of capillaries) caused by the suction is minimized or avoided.

In another embodiment according to the present invention, there are provided coilable, flexible suction bodies for stabilizing the surface of a treatment site within a body cavity of a subject. The suction bodies are designed to be mounted on the flexible tip of a steerable catheter, such as are commercially available. The invention suction body comprises an elongate, but coilable suction channel that comprises an elongate base, a flexible rim surrounding the perimeter of the base, a flexible elongate sleeve, which is usually closed at the distal end. The sleeve is attached along the perimeter of the base on the side thereof opposite to the flexible rim and has an opening at the opposite end for receiving the flexible tip of a steerable catheter. The invention suction body further comprises one or more suction ports for establishing a partial vacuum within the suction channel, and a flexible tubing in fluid communication with the one or more suction ports that can be attached to a source of partial vacuum. The invention suction body is coilable into a ring- or horseshoe-shape without loss of integrity of the suction channel.

In another embodiment according to the present invention, there are provided methods for endoscopically stabilizing a treatment site in a subject in need thereof. The invention stabilization method(s) comprise advancing the flexible tip of an invention stabilizing device in an elongate form into a body cavity of a subject, actuating the proximal steering mechanism to coil the elongate tip into a ring- or horseshoe-shape within the body cavity, holding the proximal portion of the elongate rod so that the coiled suction channel rests against the surface of the treatment site, and applying sufficient partial vacuum to the suction channel via the suction port to cause the suction channel to cling to the treatment site, thereby stabilizing the treatment site. Preferably the invention device is advanced into a body cavity of the subject through a small surgical opening, for example in a chest wall. The invention method can further comprise utilizing robotics to perform surgery on the treatment site. For example, the invention device can be used to perform by-pass surgery on a beating heart under thoracoscopic visualization without opening the chest wall.

It is an object of the present invention to provide a device for holding motionless a treatment site for an endoscopic or robotic surgery wherein the device is designed for insertion through a small surgical opening in an elongate, non-functional form and can be transformed into a functional conformation while within a body cavity of the patient.

It is a further object of the present invention to provide a device for holding motionless a treatment site, such as an anastomotic site of a coronary artery, for an endoscopic or robotic surgery without application of compression to the treatment site and without inviting scarring of the surface of the treatment site caused by application of the device.

It is a further object of the present invention to provide a practical device to hold an anastomotic site of the coronary artery motionless and bloodless during an endoscopic or robotic bypass operation by restraining the bleeding from a dissected portion of the coronary artery for anastomosis.

These and other objectives are met by the present invention, which provides an stabilizing device and method of its use for temporarily immobilizing a local area of tissue located within a body cavity accessible through a small opening, for example in the chest wall.

References and U.S. patents cited herein are hereby incorporated herein by reference in their entireties for all purposes.

BRIEF DESCRIPTION OF THE DRAWINGS

The foregoing and other aspects of the present invention will best be appreciated with reference to the detailed description of the invention in conjunction with the accompanying drawings, wherein:

FIG. 1 is a perspective drawing showing the invention stabilizing device in a coiled configuration.

FIG. 2 is a cross-section drawing of the invention stabilizing device taken through the section marked by arrows 2—2 of FIG. 1.

FIG. 3 is a perspective drawing and cut-away showing the flexible tip with flexible suction channel of the invention stabilizing device in an elongated configuration.

FIG. 4 is a cross-section drawing of the flexible tip and suction channel of the invention stabilizing device taken through the section marked by arrows 4—4 of FIG. 3.

FIG. 5 is a cross-section drawing of an alternative embodiment of the invention stabilizing device taken through the flexible tip and suction channel as in FIG. 4.

DETAILED DESCRIPTION OF THE INVENTION

Figure 6:
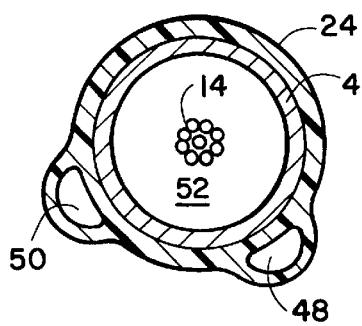
FIG. 6 is a cross-section drawing of an alternative embodiment of the invention stabilizing device with two lumens molded into the sleeve that attaches the suction channel to the rod of the invention stabilizing device.

The present invention provides a stabilizing device for stabilizing the surface of a treatment site during endoscopic or robotic surgery. The invention stabilizing device features a flexible coilable suction channel attached to a steerable rod that can be advanced into a body cavity of a subject through a small surgical opening in an open, elongate form and then transformed within the body of the subject into a coiled form. In the coiled form the suction channel is attached to the surface of an internal treatment site, such as an internal organ, by introduction of a partial vacuum into the suction channel while the suction channel is held against the surface of the treatment site. Thus, the invention stabilizing device is particularly suited for stabilizing the surface of a treatment site within a body cavity of a subject during robotic surgery.

The invention stabilizing device comprises an elongate hollow rod having a proximal end and a distal end with a flexible portion at the distal tip thereof, with the rod being sized and constructed to be advanced into a body cavity of a subject. The invention device further comprises a deflection mechanism attached to the flexible portion of the rod and to a steering mechanism associated with the proximal end of the rod for causing the flexible portion of the rod to coil into a ring- or horseshoe-shape. Attached to the flexible tip of the rod in the invention device is an elongate coilable suction channel comprising an elongate base attached along one side of the flexible tip, a flexible rim surrounding the perimeter of the base on the side opposite to the attachment of the base to the flexible tip, and one or more suction ports in the suction channel adapted to receive a partial vacuum from a remote source. Actuation of the steering mechanism in the invention device causes the suction channel to coil into a ring- or horseshoe-shape.

The rim that surrounds the base of the suction channel is continuous but is not necessarily uniform in profile or height. In describing embodiments of the invention in which the rim is not uniform, it is convenient to describe certain portions of the rim with reference to their locations in the coiled conformation. Hence the term "the outer rim portion" is used herein to describe that portion of the rim that runs around the outer perimeter (e.g., circumference) of the base when the suction channel is in the coiled conformation and the term "the inner rim portion" is used herein to describe that portion of the rim that runs around the inner perimeter In a preferred embodiment, the tip of the flared outer rim of the invention suction channel is sufficiently flexible that application of a partial vacuum to the suction channel while the outer rim of the coiled suction channel is in contact with the treatment site causes the outer rim to flatten and spread outwardly across the surface of the treatment site. By this means a soft edge for the suction channel is created to avoid bruising of the underlying tissue. As the spreading of the outer rim also enlarges the suction field to apply the partial vacuum over an increased tissue area, localized hemorrhage (e.g., of capillaries) caused by the suction is minimized or avoided.

The suction channel attached to the flexible tip of the rod is made of a soft, compliant material, such as a rubber organ elastomeric polymer, such as a silicon, a urethane, and the like, or a mixture thereof. As the suction channel is flexible, it will readily conform and cling to the shape of an uneven or contoured treatment site without application of compression on the treatment site while a partial vacuum is established and maintained within the suction channel.

The suction channel has an overall shape and flexibility such that sufficient partial vacuum can be established and maintained therein to cause the suction channel to fixedly cling to a treatment site when the suction channel is transformed into a coiled form and held against a treatment site while a partial vacuum is directed into the suction channel via the suction port, for example a partial vacuum in the range from about 100 mm Hg to about 600 mm Hg.

Generally, in the coiled conformation, rather than being curved or contoured in overall design, the flexible tip of the rod and the attached suction channel are designed to sit flush upon a planar surface, for example, with the base and tips of the inner and outer rims lying within planes. However, in an alternative embodiment, the coiled suction channel at the point of contact with the treatment surface can be contoured to conform to an uneven or contoured treatment site, such as the exterior of a human heart, and the like. Typical contoured shapes include convex, bowed, curved, and the like.

In addition, when in the coiled conformation, the coiled flexible tip of the rod and the remainder of the rod generally lie substantially in a single plane. However, in an alternative embodiment, the deflection mechanism attached to the flexible portion of the rod and to the steering mechanism associated with the proximal end of the rod are configured to cause the flexible tip of the rod and the attached suction channel to rotate into a plane that lies at an angle to the remainder of the rod as the steering mechanism is actuated (e.g., while simultaneously causing the flexible tip of the rod to coil the attached suction channel into a ring- or horseshoe-shape The deflection mechanism running between the flexible portion of the rod and the steering mechanism can be of any type known in the art, such as a cable system running down the interior of the hollow rod wherein the steering mechanism, which may be a rotatable handle, a crank or like means, is used to adjust the cable system so as to cause the flexible tip to move into a ring- or horseshoe- shape.

Generally, the flexible tip of the rod comprises an articulation section, such as a tubular covering having a pattern of circumferential slits therein which act as vertebrae for articulation of the flexible tip. The vertebrae may or may not be hinged together, and are threaded over one or more pull wires. When tension in a pull wire is increased by manipulation of the proximal steering mechanism, the vertebrae are forced together on the side associated with the particular wire, causing the assembly to bend in that direction. As many as four-ways of articulation can be achieved in such steerable endoscopic devices as described in U.S. Pat. No. 5,846,183.

For example, in one embodiment the flexible tip of the steerable catheter assembly can be selectively curved by controllably moving one of three flat sandwiched shims relative to the others by manipulation of a handle portion as steering mechanism, as described more fully in U.S. Pat. No. 5,190,050. In other embodiments, such as described more fully in U.S. Pat. No. 5,358,479, the flexible tip of the invention device can be coiled by means of a single elongated, substantially flat shim spring mounted within the flexible tip as the deflection mechanism. The shim has at least one transverse or lateral twist which causes the tip of the rod to assume a desired curvature upon operation of the steering mechanism.

In another embodiment, as described more fully in U.S. Pat. No. 4,960,134, the flexible tip of the rod in the invention device can have a lumen offset from the axis of the catheter tip, and the steering mechanism and deflection mechanism comprise a housing having a piston chamber at its distal end. A piston is mounted in the piston chamber with the proximal end of the catheter rod fixedly attached to the distal end of the piston. A puller wire is attached to the housing and extends through the piston, through and coaxial with the rod, and into the offset lumen of the catheter tip where it is attached. Movement of the piston relative to the length of the housing (or rod) results in deflection of the flexible tip. The steerable catheter assembly has a piston mounted within the hollow rod.

The invention device is sized and constructed to be advanced into a body cavity of a subject through a surgical opening no larger than is used in performance of endoscopic or robotic surgery when it is in the elongate, open conformation.

The size of the coiled suction channel is particularly adapted for attachment to an anastomotic site on the surface of a heart with the opening in the coiled base being shaped and sized to allow attachment of a coronary artery bypass graft to the anastomotic site therethrough. For example, the shape of the opening defined by the suction channel can be substantially circular, elliptical, square, and the like. If the coiled suction channel is substantially circular, the opening generally has a diameter in the range from about 1 mm to about 25 mm, preferably in the range from about 15 mm to about 20 mm, and the suction channel is referred to as having the shape of a doughnut. If substantially elliptical, the opening generally has a shorter axis in the range from about 1 mm to about 20 mm, and a longer axis in the range from about 5 mm to about 25 mm. It is not necessary that the ring-shape completely close upon itself as the steering mechanism is actuated, because the integrity of the suction channel for holding a vacuum is independent of the shape or degree of coil of the suction channel.

To ensure that bruising or scarring caused by application of the device to the treatment site is minimized, in a preferred embodiment, the portion of the rim of the suction channel that lies along the outer perimeter of the coiled base is flared and spreadable, being highly flexible and compliant to the surface of the treatment site so that application of a partial vacuum to the suction channel while the rim is in contact with the treatment site causes this portion of the rim to flatten and spread outwardly across the surface of the treatment site. This feature of the invention device is enhanced if the outer rim portion of the rim is substantially thinner at the tip than at the point of attachment to the base.

Therefore, in a preferred embodiment, the portion of the rim that lies along the outer perimeter of the coiled base, i.e., "the outer rim portion," is graduated in thickness from the point of attachment to the base to the tip of the rim and the distance from the base to the tip is greater for this portion of the rim than for the portion of the rim that lies along the inner perimeter of the coiled base (i.e., the inner rim portion). The rim is appropriately graduated in profile and height in the portions thereof between the inner and outer portions of the rim (e.g., at the ends of the suction channel in the elongate conformation) to assure that the coiled suction channel will be capable of maintaining an appropriate level of partial vacuum when in place against a treatment site and attached to a vacuum source. Further, in this preferred embodiment, when the coiled suction channel is held against a treatment site with the tip of the outer rim portion against the treatment site and a partial vacuum is directed to the suction channel via the one or more suction ports, the suction developing in the suction channel pulls the suction channel against the treatment site while the tip of the flexible outer rim portion flattens and spreads outwardly along the surface of the treatment site until the inner rim portion, which is shorter and, optionally, less flared and compliant than the tip of the outer rim portion, also comes into contact with the surface of the treatment site.

This flattening and spreading of the highly flexible outer rim portion assures that the force of the suction channel against the treatment site created by the partial vacuum therein is distributed over a much larger area of the treatment site than in embodiments wherein the outer rim portion is comparatively rigid and inflexible, hereby further minimizing damage to blood capillaries and tissue at the treatment site.

The flattening and spreading outwardly of the outer rim portion as the suction channel becomes attached to the treatment site also increases the area of the suction field. In this embodiment, therefore, the suction field of the suction channel is generally in the range from about 0.1 cm$^2$ to about 10 cm$^2$, for example, about 3.5 cm$^2$ to about 6.0 cm$^2$.

The increased size of the suction field compared to embodiments wherein the rim of the suction channel is more uniform in design reduces the vacuum pressure applied to a given area of tissue by a given source of partial vacuum, thereby further minimizing the risk that use of the invention stabilizing device or suction body will cause localized suction hemorrhage, for example, to capillaries in the suction field. The vacuum pressure (i.e., per area of tissue) established by the invention suction channel is generally in the range from about 100 mm Hg to about 600 mm Hg, and preferably about 250 mm Hg to about 450 mm Hg, depending upon the size of the suction field and the vacuum pressure of the source of partial vacuum. In any event, the minimal vacuum pressure is over the systolic blood pressure of the subject.

The suction channel can be attached to the flexible tip of the rod in the invention device in any convenient manner so as to be either permanently fixed or detachable. For example, the suction channel can be permanently affixed to the flexible tip of the rod of a steerable catheter by extending the soft, compliant material from which the suction channel is made around the flexible tip of a steerable catheter and molding it into place during manufacture, using methods and molding conditions, such as cross-linking conditions, heat and/or temperature well known in the art. Alternatively, the suction channel can be premanufactured to have a sleeve of flexible or elastic material sized to fit snugly around the flexible tip of the rod and optionally closed at the distal tip. For example, the sleeve can be attached to the perimeter of the base opposite the side of the base to which the rim of the suction channel attaches or molded contiguously therewith. The premanufactured suction channel can then be mounted onto the base either permanently or detachably.

For directing a partial vacuum into the suction channel, the invention device may further comprise a flexible suction tubing adapted for attachment to a vacuum source and in fluid communication with the one or more suction ports that open into the suction channel of the invention stabilizing device. For example, in one embodiment, the suction tubing attaches to or is joined with a suction conduit that passes through a portion of the base or rim of the suction channel and connects with the one or more suction ports. Optionally the suction tubing can be contained within a lumen in the hollow rod and connect in air tight fashion between a suction port located on the proximal exterior of the rod and the suction conduit.

Optionally, the invention device further comprises a one or more ports that exit into the opening formed by the coiled suction channel (i.e., ports that exit to the exterior of the suction channel) and a second tubing that connects with one or more ports. For example, the suction channel can have a conduit running through a portion of the base or rim through which the second tubing can be passed or with which the second tubing is connected. Preferably, the conduit is located in the inner rim portion of the suction channel. In one embodiment, the second tubing is gas tubing adapted for providing fluid-tight connection between a source of compressed gas and the ports that exit into the opening formed by the coiled suction channel. In this embodiment, the second tubing is used to provide a flow of compressed gas to the treatment site to aid in removal of fluid (e.g. blood) from the surface of the treatment site even while the suction channel is attached thereto. Optionally, the proximal portion of the gas tubing can be housed within the hollow rod of the device and attach to an exterior gas port located proximally on the rod of the device. The ability to remove fluid from the treatment site during the surgery being conducted within the opening enhances the surgeons' vision of the treatment site during the surgical procedure. In another embodiment the second tubing is a fiber optic or is adapted to house a fiber optic that is attached at the proximal end to a light source. To provide a source of light to the treatment site, the active tip of the fiber optic preferably is threaded through the conduit running through a portion of the base or rim of the suction channel (e.g., through the inner rim portion) so as to provide light into the opening via the one or more ports located on the exterior of the suction channel. The suction channel can be transparent or translucent to further enhance visibility of the treatment site while the suction channel is attached thereto.

One embodiment of the invention stabilizing device is shown in FIGS. 1–7. FIG. 1 shows the invention stabilizing device 2 in coiled configuration with suction channel 22 attached to and covering the flexible tip 26 of hollow rod 4 of the device. A rotatable handle 6 that serves as a steering mechanism is mounted at the proximal end of the hollow rod 4 and attaches to a plurality of cables 14, which attach at their distal ends to the flexible tip 26 of the device. As rotatable handle 6 is rotated, cables 14 operate as a deflection mechanism, causing the flexible tip of the rod to transform into a coiled configuration.

The flexible tip 26 of hollow rod 4 may consist of a series of short sections of rod having slits or openings therebetween (e.g. it may be of the articulated variety of steerable catheter which has a series of "vertebrae" at the flexible tip). A suction channel 8, which extends down the interior lumen 52 of hollow rod 4, exits from the center of the rotatable handle 6 for attachment to a suction source. As shown in FIGS. 4 and 5, in such an articulated variety of flexible tip, suction channel 8 extends down the interior lumen 52 of hollow rod 4 and opens into suction ports 12 in the interior of the suction channel through one or more of the circumferential slits in flexible tip 26, which act as vertebrae for articulation of the flexible tip. An optional compressed gas tubing 16, which also extends down the interior lumen 52 of hollow rod 4, is joined in fluid communication with one or more gas ports 18 through one or more of the circumferential slits in flexible tip 26. Compressed gas from a remote gas source, thus flows through gas ports 18 to provide a flow of compressed gas into opening 56 formed by the flexible tip and attached suction channel of the invention device when it is in the coiled configuration shown in FIG. 1.

Figure 7:
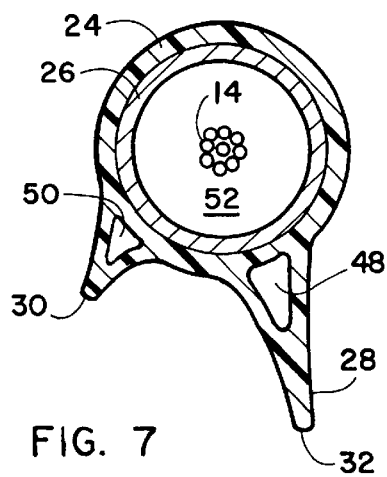
FIG. 7 is a cross-section drawing of an alternative embodiment of the invention device as in FIG. 4, but with a lumen incorporated into each of the inner and outer portions of the rim of the suction channel.

Alternatively, as shown in FIGS. 2, 6 and 7, conduit 8 is in fluid communication with suction ports 12 via channel 48, which runs through sleeve 24 and into outer rim portion 28 of the suction channel 22. In this embodiment, the suction ports 12 are small openings located in outer rim portion 28 so as to deliver a partial vacuum from conduit 8 into the suction channel 22. Similarly, an optional compressed gas tubing 16 can extend down the interior lumen 52 of hollow rod 4 and join in fluid communication with one or more gas ports 18 via channel 50 that runs through sleeve 24 and the inner rim portion 30 of the suction body 22. Optional gas ports 18 are small openings located in sleeve 24 such that compressed gas from a remote compressed gas source will be directed into the opening 26 formed when device 22 is in a coiled configuration.

In another embodiment, tubing 16 is not used to transmit gas, but is used to hold an optical fiber in optical communication with an exterior light source and a port 18 is a light port located along the exterior of the suction channel or flexible portion of the rod such that light transmitted by the light port illuminates a treatment site inside opening 26

Two embodiments of the suction channel are illustrated in FIGS. 4, 5 and 7. In the embodiment shown in FIG. 5, the inner 30 and outer 28 rim portions are substantially equivalent and attach to or are molded to be coextensive with base 10 and sleeve 24. By contrast, in an embodiment shown in FIGS. 4 and 7, the vertical height of the flared outer rim 28 (as measured from the plane of the base to that of the tip) is greater than that of the inner rim 30. In this second embodiment, the outer rim is also smoothly graduated in thickness with the point of attachment to the base being the thickest and the tip 32 being the thinnest. When the suction channel is held against a treatment site with the tip 32 of the outer rim 28 against the treatment site and a partial vacuum is directed to the suction channel via the suction port, the partial vacuum developing in the suction channel pulls the suction channel against the treatment site while the tip of the flexible outer rim flattens and spreads outwardly along the surface of the treatment site until the inner rim also comes into contact with the surface of the treatment site. An invention suction channel constructed of elastomeric polymer having the design shown in FIGS. 4 and 7 maintains the integrity of the suction channel when the suction channel is applied to a treatment site and a partial vacuum of up to 600 mm Hg is applied to the suction port.

As the negative pressure developed in the suction body is inversely proportional to the suction surface of the suction body at any given suction pressure, it can be seen that when the suction channel is at its minimum size as disclosed herein, the suction pressure developed within the suction body is greatly increased. Thus, the embodiment wherein the outer rim portion is flared and spreadable is particularly useful for preventing unwanted damage to the treatment site, such as the surface of a heart.

The elongate configuration of the suction channel is shown in perspective view from above in FIG. 3. In this configuration, the base (not visible) is elongate and rim 40 surrounds the perimeter of the of base. The coiled configuration is shown in perspective from above in FIG. 1 and in a bottom plan view in FIG. 8. In the coiled configuration, the suction channel is coiled into a substantially circular configuration, thereby creating opening 56. In this configuration, the inner rim portion 30 is that portion that lies along the inner perimeter of the coiled base, and the outer rim portion 28 is that portion that lies along the outer perimeter of the coiled base. Together, rim portions 28, 30 and 40 surround the base.

Optionally, a disposable suction reserver, such as the Medi-vac™ system (Baxter Healthcare, Deerfield, Ill.), can be interposed between the suction source and the suction channel to capture fluids collected by the suction channel.

Figure 8:
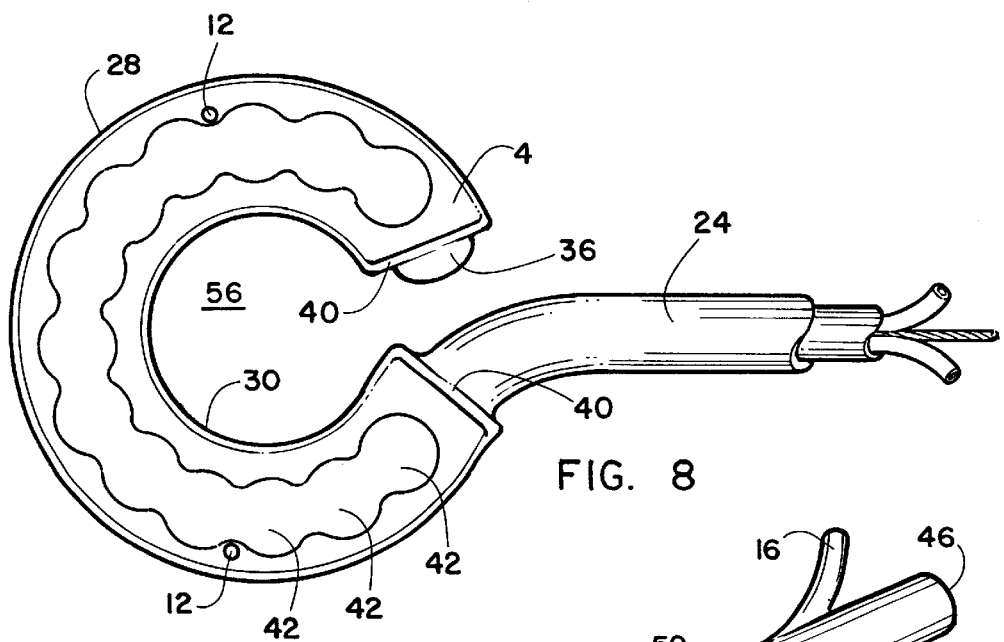
FIG. 8 is a bottom plan view of the invention stabilizing device in coiled configuration showing the interior of the suction channel with a scalloped rim.

Optionally, the base and rim of the suction channel can be shaped along the interior of the suction channel to create a series of areas wherein the partial vacuum formed upon attachment to a treatment site is greater than in adjacent areas. For example, the interior of the suction channel can be scalloped as shown in FIG. 8 so as to form a multiplicity of areas 42 along the length of the channel that function somewhat equivalent to suction cups.

Figure 9:
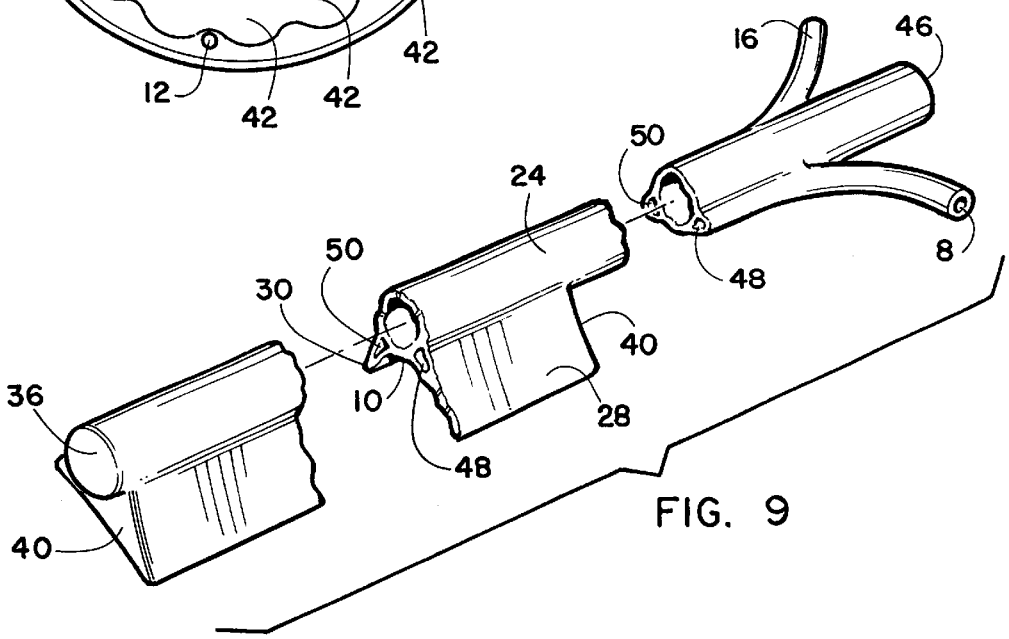
FIG. 9 is a perspective drawing showing a cut-away view of the invention suction body with sleeve for receiving the flexible tip of a steerable catheter.

In another embodiment in accordance with the present invention, described with reference to FIG. 9, there are provided coilable, flexible suction bodies, optionally disposable, for mounting on the flexible tip of a steerable catheter and for stabilizing the surface of a treatment site within a body cavity of a subject. In this embodiment, the invention suction channel can be manufactured and/or sold separately from the steerable catheter. The coilable, flexible suction body 24 of the invention, which is illustrated in FIG. 9 in the elongate configuration, comprises an elongate, but coilable, suction channel 22 comprising an elongate base 10, a flexible rim 40 with inner 28 and outer 30 rim portions surrounding the perimeter of the base, a flexible elongate sleeve 24 attached along the perimeter of the base on the side thereof opposite to the flexible rim. Sleeve 24 is closed at one end 36 but has a sleeve opening 46 at the opposite end of the elongate sleeve. The invention suction body further comprises one or more suction ports for establishing a partial vacuum within the suction channel and a flexible tubing 8 in fluid communication with the one or more suction ports. As is also shown in FIG. 9, the suction tubing 8 extends down the exterior of sleeve 24 and then joins in fluid communication with channel 48, which passes through the outer rim portion 28 of the suction body 54 wherein it joins in fluid communication with the suction ports (not shown in this Figure), which open into the suction channel.

The invention suction body, including the flexible or elastic sleeve, is made of a flexible or elastic material, preferably an elastomeric polymer, such as a silicon or a urethane, and is adapted to slide over and attach to a flexible tip of a steerable endoscopic catheter, for example by means of a friction fit. Alternatively, the suction body can be removably or permanently attached to the flexible tip of a steerable catheter by any convenient means, such as by gluing, heat fitting, binding or tying the flexible suction body to the flexible tip. Because the invention suction body is highly flexible and coilable, it can be transformed into a ring- or horseshoe-shape without loss of integrity of the suction channel.

The suction tubing is adapted for connection to a source of vacuum for introducing a partial vacuum into the suction channel. Optionally, as is further shown in FIG. 9, the invention suction body further comprises a gas tubing 16 in fluid communication with one or more gas ports located so as to direct a flow of compressed gas into an opening created when the suction body is attached to the flexible tip of a steerable catheter and transformed into a coiled configuration by operation of the steering mechanism in the catheter. As shown in FIG. 9, the gas tubing 16 joins with conduit 50, which extends down the exterior of sleeve 24 and then passes into the inner rim portion 30 of the suction body 54, wherein it joins with the gas ports, which are not shown in this Figure.

The present invention further provides methods for stabilizing a treatment site utilizing the invention stabilizing device. The invention methods comprise advancing the flexible tip of an invention stabilizing device in an elongate conformation into a body cavity of a subject, actuating the proximal deflection mechanism to coil the flexible tip into a ring- or horseshoe-shape within the body cavity, holding the proximal portion of the elongate rod so that the coiled suction channel rests against the surface of the treatment site, and applying sufficient partial vacuum to the suction channel via the one or more suction ports to cause the suction channel to cling to the treatment site, thereby stabilizing the treatment site. Preferably, the advancing of the site stabilizer into the subject's body cavity in the invention methods is via a small surgically-created opening in the body of the patient, for example an opening having dimensions in the range of about 3 mm to about 20 mm, for example from about 8 mm to about 15 mm.

The sites of treatment contemplated in the invention method include, without limitation, the surface of an internal organ, such as the heart, stomach, esophagus, gallbladder, liver, bowel, kidney, or lung of the subject, and the like. Using the invention methods and devices, the suction channel applies a stabilizing partial vacuum over a surface area in the range from about 0.1 cm$^2$ to about 10 cm$^2$ to the treatment site.

When the invention device is of the type wherein an outer rim portion is flared and spreadable, the outer rim portion will tend to flatten and spread outwardly as a partial vacuum is established within the suction channel, thus minimizing formation of localized suction hemorrhage on the surface of the treatment site.

During use, the surgeon grasps the proximal end of the rod of the invention device, which may be fitted with a handle, while actuating the proximally located steering mechanism, for example manually, to cause the flexible tip of the rod to coil into a ring- or horseshoe-shape. Optionally, the invention method can further comprise temporarily affixing the proximal portion of the rod to an exterior object, such as an operating table, to provide a further measure of stabilization to the treatment site.

The stabilizing of the treatment site generally includes applying a tension to the surface of the treatment site within the bodily cavity, which may be useful in more clearly visualizing the treatment site and/or making incisions therein, and the like. Generally, the application of a partial vacuum and the clinging of the suction channel to the treatment site also cause partial extrusion of the treatment site through the opening defined by the ring- or horseshoe-shaped suction channel, which may also enhance visibility and lend desirable attributes to the treatment site. For example, if the treatment site is an anastomotic site of a coronary artery on the surface of a beating heart, the stabilizing effect of the invention device includes substantially reducing the motion of the treatment site on the beating heart during by-pass surgery, especially during robotic by-pass surgery. Using the invention device and methods, a treatment site can readily be stabilized even on the anterior side of the beating heart.

In prior art methods of heart surgery it was necessary to "open" the chest wall, for example by median sternotomy or by thoracotomy. For example, a MIDCAB procedure was performed through a small (6- to 9 cm) left anterior chest incision in the fourth intercostal space, the left internal thoracic artery was harvested. Then the left internal thoracic artery was anastomosed to left anterior descending artery without cardio-pulmonary by-pass. However, using the invention methods and stabilizing device, the flexible tip bearing the elongate suction channel can be advanced through a small surgically created opening in the chest wall and used to stabilize a beating heart while by-pass surgery is performed robotically, for example under thoracoscopic visualization, without "opening" the chest wall.

When the stabilizing device used in the invention method is of the type having a compressed gas tubing in fluid communication with one or more gas ports located on the exterior of the suction channel so as to introduce compressed gas into an opening defined by the coiled suction channel, the invention method can further comprise directing compressed gas through the one or more gas ports into the opening to remove accumulated fluid, for example, blood, from the treatment site.

In the invention methods, the suction body is used to apply a partial vacuum over a surface area in the range from about 0.1 cm$^2$ to about 10 cm$^2$, and preferably from about 3.5 cm$^2$ to about 6.0 cm$^2$ so as to minimize formation of localized suction hemorrhage on the surface of the treatment site.

In one embodiment of the invention methods, the stabilizing device is assembled by inserting the flexible distal tip of the catheter into the opening in the sleeve of the suction body, sliding the suction body along the flexible tip of the steerable catheter, and then fixedly, but preferably removably, attaching the suction body to the flexible distal tip of the steerable endoscopic catheter, for example by friction fit. Generally, the elastic nature of the sleeve provides sufficient force against the tip of the catheter that the suction body is held firmly in place. However, it is also contemplated within the scope of the invention that such means as adhesive, ties or other suitable clips can be used to attach the suction body to the flexible tip of the catheter and/or to hold the suction body in proper alignment with respect thereto. However, the catheter used must be one that is designed to coil into a ring- or horseshoe-shape upon actuation of the steering mechanism, such as the EndoFlex™ (Genzyme Surgical Products, Cambridge, Mass.).

It will be apparent to those skilled in the art that various changes may be made in the invention without departing from the spirit and scope thereof, and therefore, the invention encompasses embodiments in addition to those specifically disclosed in the specification, but only as indicated in the appended claims.

What is claimed is:

1. A device for stabilizing the surface of a treatment site within a body cavity of a subject, said device comprising:

an elongate hollow rod having a proximal end and a distal end with a flexible portion at the distal end thereof, said rod being sized and constructed to be advanced into a body cavity of a subject;

a deflection mechanism within the hollow rod attached to the flexible portion of the rod and to a steering mechanism associated with the proximal end of the rod for causing the flexible portion of the rod to coil into a ring- or horseshoe-shape, and, an elongate coilable suction channel, said suction channel comprising an elongate base attached along one side of the flexible portion, a flexible rim surrounding the perimeter of the base on the side opposite to the attachment of the base to the flexible portion, and one or more suction ports in the suction channel in fluid communication with a partial vacuum from a remote source;

wherein actuation of the steering mechanism coils the flexible portion containing suction channel into a ring- or horseshoe-shape.

2. The device according to claim 1 wherein a portion of the rim attached along a side of the base that forms the outer periphery of the ring- or horseshoe-shape is flared and spreadable.

3. The device according to claim 2 wherein the said portion of the rim is graduated in thickness from the point of attachment to the base to the tip of the rim and the vertical distance from the base to the tip of the said portion of the rim is greater than the distance from the base to the tip of the other portion of the rim.

4. The device according to claim 2 wherein the tip of the portion of the rim is sufficiently flexible that application of a partial vacuum to the suction channel while the suction channel is in contact with the treatment site causes the portion of the rim to flatten and spread outwardly across the surface of the treatment site.

5. The device according to claim 1 wherein the coiled suction channel lies in a plane at an angle to the rod.

6. The device according to claim 1 wherein the opening defined by the ring- or horseshoe-shape of the suction channel is sized to allow surgical attachment therethrough of a coronary artery bypass graft to an anastomotic site at the treatment site.

7. The device according to claim 6 wherein the opening is substantially circular.

8. The device according to claim 7 wherein the diameter of the opening is in the range from about 1 mm to about 25 mm.

9. The device according to claim 7 wherein the diameter of the opening is in the range from about 15 mm to about 20 mm.

10. The device according to claim 6 wherein the opening is elliptical.

11. The device according to claim 10 wherein the shorter axis of the elliptical opening is in the range from about 1 mm to about 20 mm, and the longer axis of the elliptical opening is in the range from about 5 mm to about 25 mm.

12. The device according to claim 6 further comprising a gas tubing in fluid connection to one or more a gas ports located proximally on the rod exterior and to one or more gas ports adapted to deliver a flow of gas to the opening defined by the ring- or horseshoe-shape of the suction channel.

13. The device according to claim 6 further comprising an optical fiber in optical communication with a light source and a light port in optical communication with the optical fiber, said light port being located along the flexible portion of the rod or of the suction channel such that light transmitted by the light port illuminates a treatment site inside the opening.

14. The device according to claim 1 wherein the suction channel coils into a horseshoe-shape.

15. The device according to claim 1 wherein the suction field of the suction device has an area in the range from about 0.1 cm$^2$ to about 10 cm$^2$.

16. The device according to claim 15 wherein the suction field of the suction device has an area in the range from about 3.5 cm$^2$ to about 6 cm$^2$.

17. The device according to claim 1 wherein the suction channel is fabricated from an elastomeric polymer.

18. The device according to claim 17 wherein the elastomeric polymer is a silicone or a urethane.

19. The device according to claim 17 wherein the suction channel is substantially transparent.

20. The device according to claim 17 wherein the flexible portion of the rod is covered with an elongate polymeric sleeve and the base of the suction channel is attached to the rod by attachment along the sleeve.

21. The device according to claim 1 wherein the flexible portion of the rod is articulated.

22. The device according to claim 1 wherein the deflection mechanism comprises a deflection wire extending within the hollow rod from the distal tip to the steering mechanism.

23. The device according to claim 1 wherein the steering mechanism is a slide, crank, trigger or rotatable handle adapted to cause the flexible portion to coil and uncoil.

24. The device according to claim 1 wherein the device comprises at least three suction ports at spaced locations within the suction channel, which suction ports are in fluid communication with a suction tubing.

25. The device according to claim 1 wherein the suction channel is shaped to create a series of localized areas of higher partial vacuum than in adjacent areas.

26. The device according to claim 1 wherein the suction channel is contoured.

27. The device according to claim 26 wherein the optical fiber is contained within the hollow rod.

28. A method for endoscopically stabilizing a treatment site in a subject in need thereof, said method comprising:

advancing the flexible portion of a device according to claim 1 in an elongate conformation into a body cavity of a subject, actuating the proximal steering mechanism to coil the flexible portion into a ring- or horseshoe-shape within the body cavity, holding the proximal portion of the elongate rod so that the coiled suction channel rests against the surface of the treatment site, and applying sufficient partial vacuum to the suction channel via the suction port to cause the suction channel to cling to the treatment site, thereby stabilizing the treatment site.

29. The method according to claim 28 wherein a portion of the rim attached along a portion of the base that forms the outer periphery of the ring-shape or horseshoe-shape is flared and spreadable and wherein the said portion of the rim flattens and spreads outwardly as a partial vacuum is established within the suction channel.

30. The method according to claim 28 wherein the advancing of the endoscopic site stabilizer is via a surgically-created opening in the body of a patient.

31. The method according to claim 28 further comprising temporarily affixing the proximal portion of the rod to an exterior object.

32. The method according to claim 28 wherein the stabilizing includes applying a tension to the surface of the treatment site within the bodily cavity.

33. The method according to claim 28 wherein the application of a partial vacuum causes partial extrusion of the treatment site through the opening defined by the ring- or horseshoe-shaped suction channel.

34. The method according to claim 33 wherein the coiled suction channel is sized to allow surgical manipulation of the treatment site through the opening defined by the coiled suction channel while the suction channel is attached to the treatment site.

35. The method according to claim 28 wherein the treatment site is an anastomotic site of a coronary artery on the surface of a beating heart and the stabilizing involves substantially reducing the motion of the treatment site on the beating heart during by-pass surgery.

36. The method according to claim 35 wherein the surface of the beating heart is stabilized during robotic surgery.

37. The method according to claim 35 wherein the treatment site is located on the anterior side of the beating heart.

38. The method according to claim 35 wherein by-pass surgery is conducted under thoracoscopic visualization without opening the chest wall.

39. The method according to claim 28 wherein the steering mechanism is manually actuated.

40. The method according to claim 28 wherein the device further comprises a compressed gas tubing in fluid communication between a gas source and one or more gas ports adapted to provide a flow of compressed gas into the opening formed by the coiled suction channel.

41. The method according to claim 28 wherein the suction channel applies a partial vacuum over a surface area in the range from about 0.1 cm$^2$ to about 10 cm$^2$.

42. The method according to claim 28 wherein formation of localized suction hemorrhage on the surface of the treatment site is minimized.

43. The method according to claim 28 wherein the treatment site is located on the surface of an internal organ.

44. The method according to claim 43 wherein the internal organ is the heart, stomach, esophagus, gallbladder, liver, bowel, kidney, or lung of the subject.

* * * * *